(12) United States Patent
Lafontaine

(10) Patent No.: US 7,189,227 B2
(45) Date of Patent: *Mar. 13, 2007

(54) CRYO BALLOON

(75) Inventor: Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 143 days.

This patent is subject to a terminal disclaimer.

(21) Appl. No.: 11/085,763

(22) Filed: Mar. 21, 2005

(65) Prior Publication Data
US 2005/0182395 A1   Aug. 18, 2005

Related U.S. Application Data

(63) Continuation of application No. 10/126,027, filed on Apr. 19, 2002, now Pat. No. 6,989,009.

(51) Int. Cl.
*A61M 29/02*   (2006.01)

(52) U.S. Cl. .................................................... 606/20

(58) Field of Classification Search ............ 606/20–26, 606/191–200
See application file for complete search history.

(56) References Cited

U.S. PATENT DOCUMENTS

| | | | |
|---|---|---|---|
| 3,125,096 A | 3/1964 | Antiles et al. | |
| 3,712,306 A | 1/1973 | Bryne | |
| 4,278,090 A | 7/1981 | van Gerven | |
| 4,280,499 A | 7/1981 | Sguazzi | |
| 4,784,133 A | 11/1988 | Mackin | |
| 4,860,744 A | 8/1989 | Johnson et al. | |
| 4,901,735 A * | 2/1990 | von Berg | 600/561 |
| 5,019,042 A | 5/1991 | Sahota | |
| 5,078,713 A | 1/1992 | Varney | |
| 5,108,390 A | 4/1992 | Potocky et al. | |
| 5,139,496 A | 8/1992 | Hed | |
| 5,147,355 A | 9/1992 | Friedman et al. | |
| 5,190,540 A | 3/1993 | Lee | |
| 5,281,215 A | 1/1994 | Milder | |
| 5,334,181 A | 8/1994 | Rubinsky et al. | |
| 5,334,193 A | 8/1994 | Nardella | |
| 5,335,669 A | 8/1994 | Tihon et al. | |
| 5,342,301 A | 8/1994 | Saab | |

(Continued)

FOREIGN PATENT DOCUMENTS

GB    1019028    2/1966

(Continued)

OTHER PUBLICATIONS

Hendry et al., "Argon Beam Coagulation Compared with Cryoablation of Ventricular Subenocardium," *Annals of Thoracic Surgery*, 1993, 55(1):135-139, Abstract only.

(Continued)

*Primary Examiner*—Roy D. Gibson
*Assistant Examiner*—Aaron Roane
(74) *Attorney, Agent, or Firm*—Fish & Richardson P.C.

(57) ABSTRACT

Devices and methods for performing cryo therapy, cryo ablation or cryoplasty. A cryo therapy apparatus may comprise an elongate shaft, a cooling member disposed at the distal end of the shaft, and a pressure gauge coupled to the cooling member.

20 Claims, 4 Drawing Sheets

U.S. PATENT DOCUMENTS

| | | | |
|---|---|---|---|
| 5,417,689 A | 5/1995 | Fine | |
| 5,423,807 A | 6/1995 | Milder | |
| 5,443,470 A | 8/1995 | Stern et al. | |
| 5,454,807 A | 10/1995 | Lennox et al. | |
| 5,501,681 A | 3/1996 | Neuwirth et al. | |
| 5,520,682 A | 5/1996 | Baust et al. | |
| 5,536,252 A | 7/1996 | Imran et al. | |
| 5,624,392 A | 4/1997 | Saab | |
| 5,674,218 A | 10/1997 | Rubinsky et al. | |
| 5,807,391 A | 9/1998 | Wijkamp | |
| 5,860,938 A | 1/1999 | LaFontaine et al. | |
| 5,868,735 A | 2/1999 | LaFontaine | |
| 5,902,299 A | 5/1999 | Jayaraman | |
| 5,957,917 A | 9/1999 | Doiron et al. | |
| 5,964,714 A | 10/1999 | LaFontaine | |
| 5,968,059 A | 10/1999 | Ellis et al. | |
| 5,971,979 A | 10/1999 | Joye et al. | |
| 6,012,457 A | 1/2000 | Lesh | |
| 6,024,740 A | 2/2000 | Lesh et al. | |
| 6,106,518 A | 8/2000 | Wittenberger et al. | |
| 6,179,835 B1 | 1/2001 | Panescu et al. | |
| 6,193,644 B1 | 2/2001 | Dobak, III et al. | |
| 6,283,959 B1 | 9/2001 | Lalonde et al. | |
| 6,290,696 B1 | 9/2001 | Lafontaine | |
| 6,355,029 B1 * | 3/2002 | Joye et al. | 606/21 |
| 6,595,988 B2 * | 7/2003 | Wittenberger et al. | 606/21 |
| 2002/0032438 A1 | 3/2002 | Lafontaine | |
| 2002/0045894 A1 | 4/2002 | Joye et al. | |
| 2002/0091378 A1 | 7/2002 | Dobak, III et al. | |
| 2002/0151880 A1 | 10/2002 | Lafontiane | |

FOREIGN PATENT DOCUMENTS

| | | |
|---|---|---|
| GB | 2 336 782 A | 11/1999 |
| GB | 2 337 000 A | 11/1999 |
| WO | WO 97/12557 | 4/1997 |
| WO | WO 99/27862 | 6/1999 |
| WO | WO 00/47118 | 8/2000 |
| WO | WO 02/07625 | 1/2002 |
| WO | WO 02/07628 | 1/2002 |
| WO | WO 02/83196 | 10/2002 |

OTHER PUBLICATIONS

Fujino et al., "Histologic Study of Chronic Catheter Cryoablation of Atrioventricular Conduction in Swine," *American Heart Journal*, 1993, 125(6):1632-1637.

Gaer et al., "Intractable Chest Pain in Cardiomyopathy: Treatment by a Novel Technique of Cardiac Cryodenervation with Quantitative Immunohistochemical Assessment of Success," *Br. Heart J.*, 1993, Abstract only.

Hunt et al., "Fractures in Cryopreserved Arteries," *Cryobiology*, 1994, 31:506-515.

Abstract entitled "Cardiac Rhythm Disturbances due to Caval Occlusion During Hepatic Cryosurgery," *Cryobiology*, Oct. 1994.

Coger et al., " Preservation Techniques for Biomaterials," *The Biomedical Engineering Handbook*, 1995, 8 pages.

Abstract entitled "Percutaneous Serial Catherization in Swine: a Practical Approach", *Journal of Investigative Surgery*, Mar.-Apr. 1995.

Schilling et al., "Nature of the Vehicle for Cryopreservation of Human Peripheral Veins: Preservation of Reactivity to Pharmacological Stimuli,"*Cryobiology*, 1995, 32:327-333.

Nataf et al., "Effect of Cold Anoxia and Cryopreservation on Metabolic and Contractile Functions of Human Mannary Artery," *Cryobiology*, 1995, 32:327-333.

Abstract entitled "Cox Maze Operation Without Cryoablation for the Treatment of Chronic Atrial Fibrillation", *Annals of Thoracic Surgery*, Aug. 1995, Abstract only.

Abstract entitled "Renal Cryoablation in a Canine Model," *Urology*, May 1996.

Mazur, Physical-Chemical Factors Underlying Cell Injury in Cryosurgical Freezing, *Cryosurgery*, pp. 32-51, published on date even with or prior to Jan. 12, 1999.

Cahan, "Five Years of Cryosurgical Experience: Benign and Malignant Tumors with Hemorrhagic Conditions," *Cryosurgery*, pp. 388-391, published on date even with or prior to Jan. 12, 1999.

Zacarian, "Cryosurgery of Tumors of the Skin and Oral Cavity," 5 pages, published on date even with or prior to Jan. 12, 1999.

Fuller et al., "Clinical Applications of Cryobiology," 4 pages, published on date even with or prior to Jan. 12, 1999.

Morris et al., "Effects of Low Temperatures on Biological Membranes," 2 pages, published on date even with or prior to Jan. 12, 1999.

Article entitled "Prostate Cryosurgery now Reimbursable in Southern California," *Healthcare Technology Management*, published on date even with or prior to Jan. 12, 1999, Abstract only.

* cited by examiner

CRYO BALLOON

CROSS-REFERENCE TO RELATED APPLICATIONS

This is a continuation application of U.S. application Ser. No. 10/126,027, which was filed Apr. 19, 2002, which issued as U.S. Pat. No. 6,989,009 on Jan. 24, 2006, and which is entitled "Cryo Balloon." The disclosure of the prior application is incorporated herein by reference in its entirety.

FIELD OF THE INVENTION

The present invention pertains generally to the field of cryo therapy. More particularly, the present invention pertains to cryo ablation catheters for use in causing cold-induced necrosis and cryoplasty catheters for use in causing apoptosis to prevent restenosis.

DESCRIPTION OF THE RELATED ART

A number of medical conditions may be treated using ablative techniques or devices. Ablative techniques, generally, result in destroying the function of abnormal tissue at an area of interest. Destroying the function of the abnormal tissue may result in an efficacious treatment for a medical condition. For example, atrial fibrillation may be the result of abnormal electrical activity in the left atrium and the pulmonary vein, and may be treatable by ablation of the abnormal tissue within the left atrium and/or the pulmonary vein.

Atrial fibrillation is a serious medical condition that is the result of abnormal electrical activity within the heart. This abnormal activity may occur at regions of the heart including the sino-atrial (SA) node, the atriovenricular (AV) node, the bundle of His, or within other areas of cardiac tissue. Moreover, atrial fibrillation may be caused by abnormal activity within a isolated focal center within the heart. It is believed that these foci can originate within the pulmonary vein, particularly the superior pulmonary veins.

Minimally invasive techniques have been described that use ablation catheters to target the pulmonary vein with the hope of ablating foci having abnormal electrical activity. The techniques typically are characterized by application of energy to cause lesions within the foci or other areas possessing abnormal electrical activity.

Some ablation devices utilize radio frequency (RF) energy for ablation. The RF energy devices may be used to ablate an area of interest with heat. The use of RF energy for ablation may, however, lead to untoward healing responses such as collagen build up at the area of interest after treatment. Moreover, RF ablation of within an atrium may decrease atrial output. A need, therefore, exists for ablative devices and methods that include improved healing responses.

An alternative treatment strategy has been developed that uses cooling energy for ablation. This method, termed cryoplasty or cryo therapy, may be used to cool the lesion to freeze a portion of the affected area. For example, cryoplasty may be used to freeze a lesion within a blood vessel to induce apoptosis or remodeling that might otherwise lead to restenosis or recoil. In addition to its potential utility in preventing and slowing restenosis and addressing recoil, cryo therapy may be used for ablation techniques. For example, cryo therapy may be efficacious in varicose vein treatment of incompetent valves, valvular disease, mitral valve regurgitation therapy, atrial fibrillation, gastric reflux disease, gastro esophageal reflux disease, GURD, esophageal disease, cancer treatment including stomach or uterine cancer, etc.

SUMMARY OF THE INVENTION

The present invention pertains to cryo therapy catheters. More particularly, the present invention comprises a cryo therapy device including a pressure gauge to monitor the pressure within an inflatable portion of the cryo therapy apparatus and a pressure release tube that may comprise a conduit for coolant to escape should pressure become too great. The present invention can be used to ablate tissue (such as abnormal tissue within the pulmonary vein), ablate tissue in order prevent restenosis in the vasculature and cardiac tissue, and ablate other target regions where cryo therapy may have beneficial effects.

The cryo therapy device may include an elongate shaft having a cooling member disposed at the distal end thereof. The pressure gauge may be coupled to the cooling member. The pressure gauge may comprise a strain gauge that may include a direct or indirect measure of pressure within the inner member that may be quantified directly or indirectly by a clinician. In an alternate embodiment, the pressure gauge may comprise a horizontal strain gauge. A horizontal strain gauge is substantially similar to the strain gauge detailed above except that it may be disposed at the inner member in a differing pattern. The pressure gauge may also be an optical, piezoelectric, magnetic, or mechanical micro sensors disposed within the cryo chamber.

The pressure release tube has a proximal end, a distal end, and a lumen extending therethrough. A removable valve may be disposed at the proximal end of the pressure release tube. The removable valve may be removed from the pressure release tube to allow pressure to escape from the inner member. In addition, a pressure-sensitive valve may be disposed at the distal end of the pressure release tube. The pressure-sensitive valve is understood to be a valve disposed at the distal end that will provide an opening to the lumen of the pressure release tube if the pressure within the inner member becomes too great. The pressure relief valve may also be a pressure relief mechanism such as a puncture device such as an RF relief cutter, or alternatively a mechanical needle to puncture the balloon and create a controlled release of gas. The controlled release of gas may be into an isolation chamber surrounding the cryo chamber.

DETAILED DESCRIPTION OF THE PREFERRED EMBODIMENTS

Figure 1:
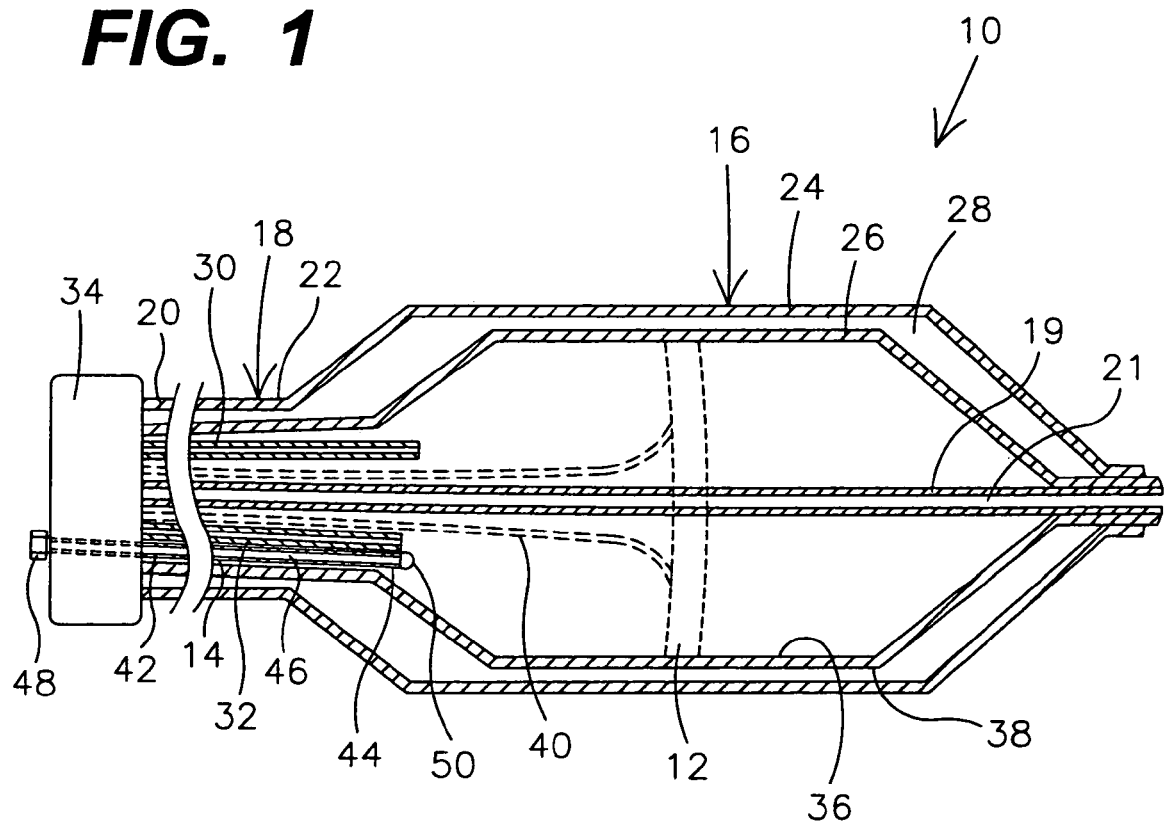
FIG. 1 is a cross-section of a cryo therapy device having a pressure gauge and a pressure release tube.

The following description should be read with reference to the drawings wherein like reference numerals indicate like elements throughout the several views. The detailed description and drawings represent select embodiments and are not intended to be limiting.

FIG. 1 is a cross-section of a cryo therapy device 10 having a pressure gauge 12 and a pressure release tube 14. Pressure gauge 12 is coupled to a cooling member 16, for example on an inner member 26. Pressure gauge 12 may be used to quantify pressure within cooling member 16. Cooling member 16 is coupled to an elongate shaft 18. In addition, at least a portion of pressure relief tube 14 is disposed within cooling member 16. Pressure relief tube 14 may be used to release inflation/cooling media from cooling member 16. This could be done, for example, when the pressure in cooling member 16 as detected by gauge 12 is in excess of a desired limit.

Cryo therapy device 10 may use heat transfer to perform a number of procedures including pulmonary vein ablation, pulmonary artery ablation, atrial fibrillation, arrhythmia, and other conditions. Moreover, cryo therapy device 10 may be used to prevent restenosis in the vasculature (including the pulmonary artery and vein), cardiac tissue (including atria and ventricles), and other target regions where cryoplasty may have beneficial effects.

Shaft 18 includes a proximal end 20 and a distal end 22. Shaft 18 may be generally tubular and may be comprised of material including, but not limited to, metals, stainless steel, nickel alloys, nickel-titanium alloys, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether block amide (PEBA), polyether-ether ketone (PEEK), polyimide, polyamide, polyphenylene sulfide (PPS), polyphenylene oxide (PPO), polysufone, nylon, perfluoro(propyl vinyl ether) (PFA), and combinations thereof. In addition, a guidewire tube 19 having a guidewire lumen 21 extending therethrough (and through cooling member 16) may be disposed within shaft 18.

Cooling member 16 may be disposed at a distal end 22 of shaft 18. Cooling member 16 may comprise an outer member 24, inner member 26, and an annular space 28 therebetween. As an alternate feature, a vacuum source can be fluidly connected to device 10 to evacuate space 28. Both outer member 24 and inner member 26 can be, for example, balloons comprised of polyether block amide (PEBA). Outer member 24 and inner member 26 can have a burst pressure, for example, of about 6 to 24 atmospheres. Polyether block amide is commercially available from Atochem Polymers of Birdsboro, Pa., under the trade name PEBAX. Alternatively, cooling member 16 may be comprised of materials listed above.

Inner member 26 is in fluid communication with a coolant source. For example, the coolant source may be coupled to inner member 26 by an inflation tube 30 and a drain tube 32 each disposed within shaft 18. The inflation tube and the drain tube are substantially similar to analogous objects disclosed within U.S. Pat. No. 5,868,735 to Lafontaine and U.S. patent application Ser. No. 09/849,892 to Lafontaine, the entire disclosures of which are hereby incorporated by reference. Outer member 24 may contain coolant which may escape from inner member 26. Cryo therapy device 10 may further comprise additional elements and features disclosed within the above-incorporated references.

Proximal end 20 of elongate shaft 18 may be connected to a manifold 34. Manifold 34 may comprise a coolant source. For example, manifold 34 may comprise a coolant source coupled to inner member 26 via inflation tube 30. Additionally, manifold 34 may comprise means for actuating (i.e., inflating) inner member 26 adapted to connect to an inflation pump.

Inner member 26 may further comprise an inner surface 36 and an outer surface 38. Pressure gauge 12 may be disposed at outer surface 38. In an alternative embodiment, pressure gauge 12 may be disposed at inner surface 36. Pressure gauge 12 may be connectable to manifold 34 by a connector 40.

Pressure gauge 12 may comprise, for example, a strain gauge, fuse link, optical transmitter with a fiber optic output, etc. In general, the length of pressure gauge 12 may be altered by increasing the size and/or pressure of inner member 26 (e.g., by inflation with a coolant). Therefore, the strain of pressure gauge 12 may comprise a direct or indirect measure of pressure within inner member 26. The fuse link embodiment would measure pressure in a threshold manner. For example, when the balloon pressure expands the balloon to a size that breaks the link, the interruption of conductivity would be sensed and indicate excessive pressure. The optical transmitter with a fiber optic output embodiment would allow a user to visualize inner member 26 to determine if pressure should be altered. For example, connector 40 may comprise a fiber optic output and manifold 34 may include a optical transmitter. In general, optical visualization may be accomplished in any manner that is known in the art.

Means for quantifying strain and/or stress may include an analog reading or display, a digital reading or display, a connector for coupling to a computerized system for quantifying strain, a computerized system for processing other data, and combinations thereof. A person of ordinary skill in the art would be familiar with these and alternative means for quantifying strain according to multiple embodiments of the invention and converting the strain measurement to a pressure measurement.

Pressure release tube 14 may comprise a proximal end 42, a distal end 44, and a lumen 46 extending therethrough. Pressure release tube 14 may be comprised of materials similar to those listed above. Pressure release tube 14 may comprise a conduit for a coolant to escape from inner member 26 if pressure therein exceeds a desired limit. For example, inner member 26 may comprise a burst pressure of 8 atmospheres. Pressure release tube 14 may be in fluid communication with inner member 26. If the pressure within inner member 26 approaches the burst pressure, coolant may be removed from inner member 26 through pressure release tube 14.

A removable valve 48 may be disposed at proximal end 42 of pressure release tube 14. According to this embodiment, if pressure within inner member 26 approaches a desired limit, for example, the burst pressure, removable valve 48 may be removed from pressure release tube 14 to allow pressure to escape inner member 26. Removable valve 48 may be located proximate manifold 34 so that it may be available to a user of cryo therapy device 10.

In use, pressure within inner member 26 may be measured by pressure gauge 12 and may be quantified. The amount of pressure within inner member 26 may be available to a clinician performing a medical procedure. If the pressure becomes too great within inner member 26 or approaches the burst pressure thereof, the clinician may remove removable valve 48 from pressure release tube 14. Removing removable valve 48 from pressure release tube 14 will reduce pressure within inner member 16.

A pressure-sensitive valve 50 may be disposed at distal end 44 of pressure relief tube 14. Pressure-sensitive valve 50 is understood to be a valve disposed at distal end 44 that will provide an opening to lumen 46 if the pressure within inner member 26 becomes too great (e.g., approaches a desired limit, such as the burst pressure of inner member 26). Pressure-sensitive valve 50 may be used with or without removable valve 48.

Figure 2:
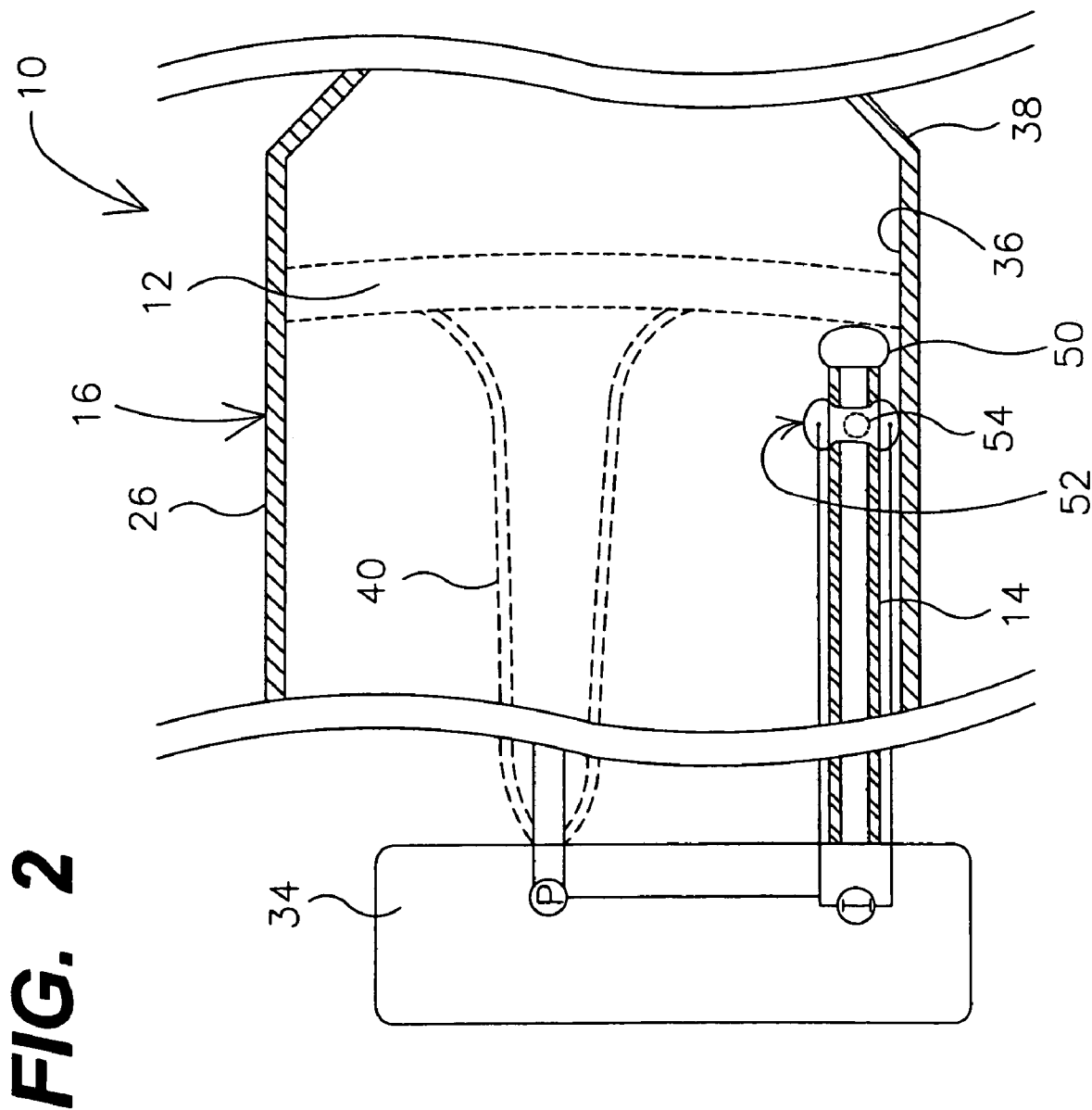
FIG. 2 is a partial cross-section of a cryo therapy device having a fuse link coupled to the pressure relief tube.

FIG. 2 is a partial cross-section of cryo therapy device 10 having a fuse link 52 coupled to pressure relief tube 14. Fuse link 52 may be used independently or in conjunction with valve 48, cap 50, or both. Fuse link 52 includes a portion that covers a vent opening 54 within pressure relief tube 14 and is coupled to pressure sensor (P) such that when pressure exceeds a threshold level, current (I) is increased within fuse link 52 sufficient to burn fuse link 52 and expose vent opening 54, which allows cooling chamber 16 to be vented. The pressure sensor may comprise a number of objects such as strain gauge 12, a piezoelectric MEMS (microelectromechanical systems) sensors, a fiber optic sensor, optical sensors, walls of cooling chamber 16, magnetic or mechanical micro sensors disposed within cooling chamber 16, etc. It should be noted that FIG. 2 depicts the pressure gauge as being connected to connector 40 of pressure gauge 12 at manifold 34. However, any of the pressure sensors listed above may be substituted and coupled to fuse link 52 at any convenient location such as at manifold 34, within cooling chamber 16, etc.

The pressure sensor and fuse link 52 may be coupled by an electrical circuit. For example, the pressure signal may be amplified and then compared with a pressure threshold at a second amplifier. The pressure threshold may be set a desired level near and/or less than the burst pressure of inner member 26. Pressure in excess of the burst pressure may be further amplified (for example, to correct or increase the signal) an go on burn fuse link 52 and expose opening 54. It can be appreciated that other suitable configurations of electrical circuits may be substituted without departing from the spirit of the invention.

Figure 3:
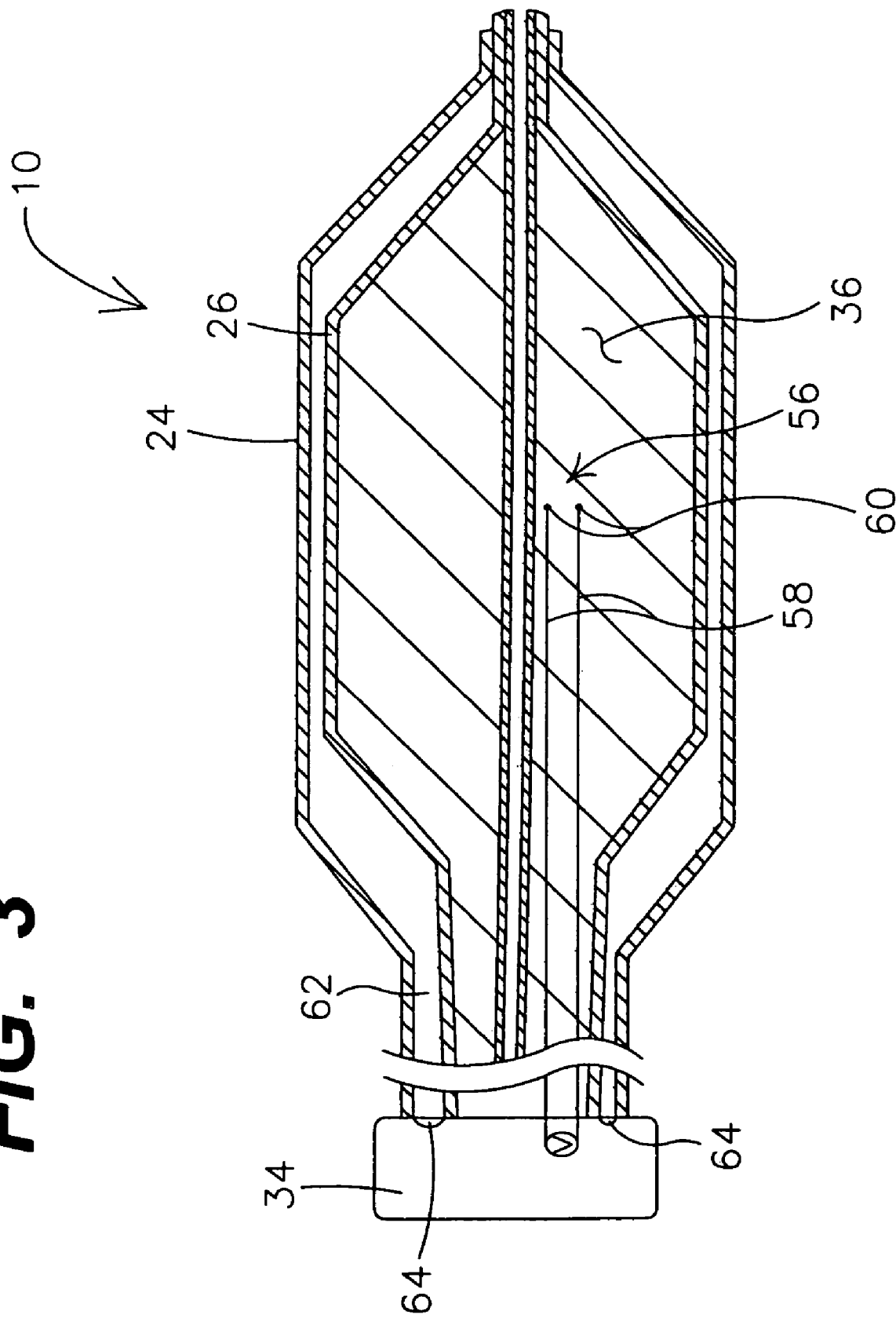
FIG. 3 is a partial cross-section of a cryo therapy device having a relief cutter coupled to the inner surface of the inner member of the cooling chamber.

FIG. 3 is a partial cross-section of cryo therapy device 10 having a relief cutter 56 coupled to inner surface 36 of inner member 26. Relief cutter 56 may be used independently or in conjunction with valve 48, cap 50, fuse link 52, or combinations thereof. Relief cutter 56 may be comprised of one or more wires 58 (e.g., about 0.007 inches in diameter, more, or less) disposed along inner surface 36 of inner member 26. For example, relief cutter 56 may comprise two parallel insulated wires installed on inner surface 36. The wires may be spaced a distance (e.g., 0.02 about inches, more, or less) and be connected to source of potential energy (V) such as a radio-frequency (RF) energy source, a laser energy source, an ultrasonic energy source, etc. Electrodes 60 may be disposed on the ends of wires 58 for generating a spark or other cutting means. In an alternative embodiment, relief cutter 56 may comprise a mechanical puncture device such as a needle, a pull wire, or other suitable object.

To actuate relief cutter 56, energy (RF) is applied to wires 58, which creates a spark or other suitable cutting means at electrodes 60. The spark can result in a relatively small hole (e.g., about 0.25 inches in diameter, more, or less) within inner member 26. The hole allows coolant contained within inner member 26 to be vented out into outer member 24 and out of the catheter through an outer lumen 62. Outer lumen 62 is in fluid communication with manifold 34 so that any vented coolant may be contained therein. For example, manifold 34 may includes an opening 64 for cooling to be vented through and into a holding vessel within manifold 34. It is believed that relief cutter 56 will create small holes within inner member 26 without causing further tearing or dissection of inner member 26.

Relief cutter 56, may be connected to a pressure gauge (e.g., strain gauge 12 and others described above) via an electrical circuit. This may allow automated actuation of relief cutter 56 in the event of pressure approaching the burst pressure of inner member 26. For example, the energy source may be switched on by an amplified signal from the pressure gauge (similar to how the pressure signal actuates fuse link 52).

Figure 4:
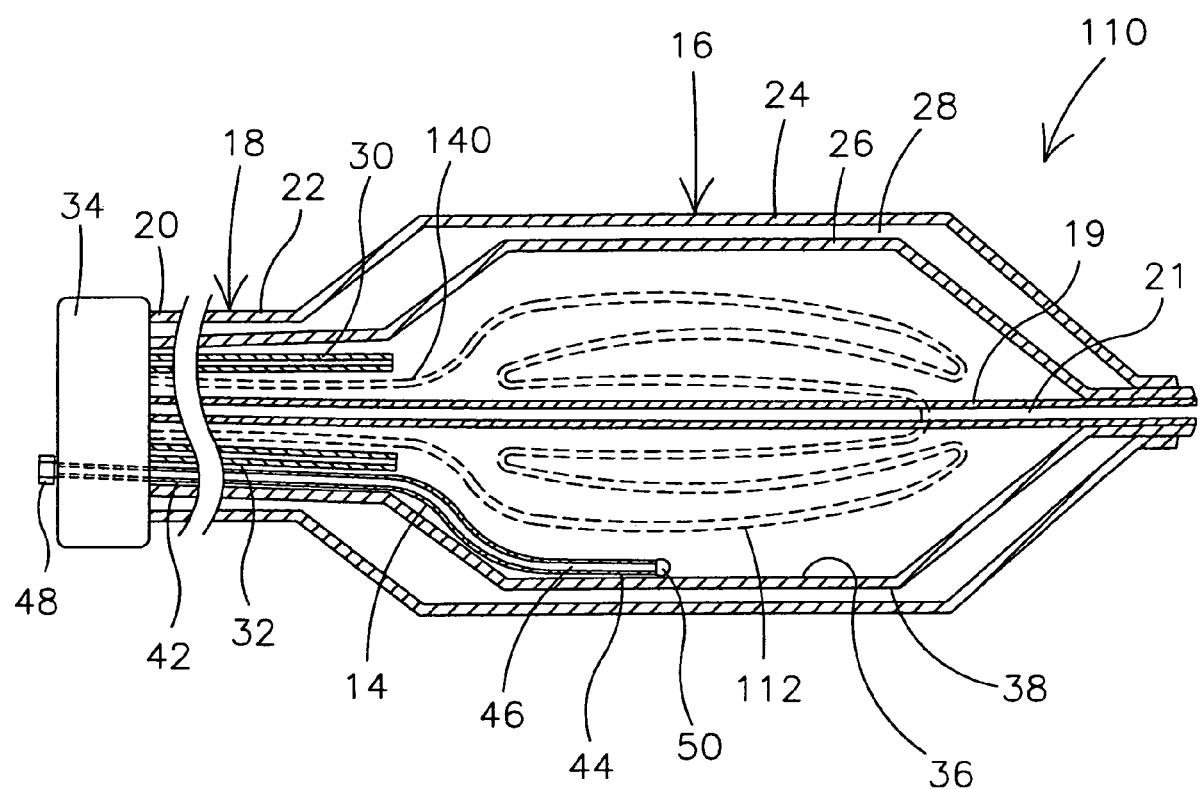
FIG. 4 is a cross-section of a cryo therapy device having an alternate pressure gauge and a pressure release tube.

FIG. 4 is a cross-section of cryo therapy device 110 having an alternate pressure gauge 112 and a pressure relief tube 14. Cryo therapy device 110 is substantially similar to cryo therapy device 10 except that pressure gauge 112 comprises a horizontal strain gauge or fuse link. A horizontal strain gauge is substantially similar to the strain gauge detailed above except that it may be disposed at inner member 26 in a differing pattern. The differing pattern may be capable of quantifying a different distribution of pressure within inner member 26. It can be appreciated that any number of differing shapes or patterns may be used for pressure gauge 112 without departing from the spirit of the invention.

Similar to what is disclosed above cryo therapy device 110 may further include pressure relief tube 14. Further, device 110 may include fuse link 52 and/or relief cutter 56. Fuse link 52 and/or relief cutter 56 may be used in conjunction with pressure gauge 112 or with other objects or configurations described above.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

The invention claimed is:

1. A cryo therapy device, comprising:
   an elongate shaft having a proximal end and a distal end;
   a cooling member disposed at the distal end, wherein the cooling member comprises an outer member and an inflatable inner member; and
   a strain sensor attached to a surface of the inner member to provide an indication of the strain on the surface.

2. The cryo therapy device of claim 1, wherein the surface is an inner surface of the inner member.

3. The cryo therapy device of claim 1, wherein the surface is an outer surface of the inner member.

4. The cryo therapy device of claim 1, wherein the strain sensor provides an output signal corresponding to a strain on the surface.

5. The cryo therapy device of claim 1, wherein the strain sensor comprises a strain gauge.

6. The cryo therapy device of claim 1, wherein the strain sensor comprises a fuse link.

7. The cryo therapy device of claim 1, further comprising a relief cutting means for relieving the pressure in the inner member.

8. The cryo therapy device of claim 7, wherein the relief cutting means is operable to relieve pressure in the inner member when the strain sensor detects that a strain on the surface of the inner member exceeds a predetermined threshold.

9. The cryo therapy device of claim 8, wherein the relief cutting means comprises a radio-frequency energy source.

10. The cryo therapy device of claim 8, further comprising a relief valve disposed within the inner member.

11. The cryo therapy device of claim 10, wherein the relief cutting means comprises a laser energy source in optical communication with the relief valve by fiber optic cable.

12. The cryo therapy device of claim 10, wherein the relief cutting means comprises an ultrasonic energy source in mechanical communication with the relief valve.

13. The cryo therapy device of claim 1, further comprising a pressure release tube having a proximal end, a distal end, and a lumen extending therethrough.

14. The cryo therapy device of claim 13, wherein the pressure release tube is in fluid communication with the inner member.

15. The cryo therapy device of claim 14, wherein the pressure release tube further comprises a removable valve disposed at the proximal end thereof.

16. The cryo therapy device of claim 13, wherein the pressure release tube further comprises a pressure-sensitive valve disposed at the distal end thereof.

17. The cryo therapy device of claim 13, further comprising a fuse link coupled to the pressure release tube.

18. The cryo therapy device of claim 17, wherein the fuse link is disposed over an opening within the pressure relief tube and wherein the fuse link is coupled to the strain sensor.

19. A method, comprising:

providing an elongate shaft having a proximal end and a distal end;

disposing a cooling member at the distal end, wherein the cooling member comprises an outer member and an inflatable inner member; and attaching a strain sensor to a surface of the inner member to provide an indication of the strain on the surface.

20. The method of claim 19, wherein the strain sensor comprises a strain gauge.

* * * * *